(12) United States Patent
Burrow et al.

(10) Patent No.: US 7,753,051 B2
(45) Date of Patent: Jul. 13, 2010

(54) FACE MASK STRAP SYSTEM

(75) Inventors: Kevin Burrow, Carmel, IN (US);
Thomas McGrail, Cicero, IN (US);
Dennis Irlbeck, Noblesville, IN (US);
Stefany Bouchez, Carmel, IN (US)

(73) Assignee: King Systems Corporation,
Noblesville, IN (US)

( * ) Notice: Subject to any disclaimer, the term of this patent is extended or adjusted under 35 U.S.C. 154(b) by 1092 days.

(21) Appl. No.: 11/378,816

(22) Filed: Mar. 17, 2006

(65) Prior Publication Data

US 2006/0207600 A1    Sep. 21, 2006

(51) Int. Cl.
*A62B 18/08* (2006.01)

(52) U.S. Cl. ............... 128/207.11; 128/206.21; 128/206.28; 128/206.27

(58) Field of Classification Search ............ 128/207.11, 128/206.21, 205.25, 206.12, 206.14, 205.29, 128/206.27, 206.28
See application file for complete search history.

(56) References Cited

U.S. PATENT DOCUMENTS

| | | | |
|---|---|---|---|
| 3,556,097 A | 1/1971 | Wallace | |
| 3,815,596 A | 6/1974 | Keener | |
| 3,856,051 A | 12/1974 | Bain | |
| 4,007,737 A | 2/1977 | Paluch | |
| 4,084,949 A | 4/1978 | Biggins | |
| 4,164,942 A | 8/1979 | Beard et al. | |
| 4,188,946 A | 2/1980 | Watson et al. | |
| 4,226,234 A | 10/1980 | Gunderson | |
| 4,232,667 A | 11/1980 | Chalon et al. | |
| 4,265,235 A | 5/1981 | Fukunaga et al. | |
| 4,300,549 A | 11/1981 | Parker | |
| 4,323,063 A | 4/1982 | Fisichella | |
| 4,347,205 A | 8/1982 | Stewart | |
| 4,414,973 A | 11/1983 | Matheson et al. | |
| 4,463,755 A | 8/1984 | Susuki | |
| D277,513 S | 2/1985 | Parsons et al. | |
| 4,589,408 A | 5/1986 | Singer | |
| 4,596,246 A | 6/1986 | Lyall | |
| 4,606,341 A | 8/1986 | Hubbard et al. | |

(Continued)

OTHER PUBLICATIONS

Prior art Face Mask and Strap System shown at Fig. 7 of present application and discussed at paragraphs 47-53 of instant application.

(Continued)

*Primary Examiner*—Justine R Yu
*Assistant Examiner*—Colin Stuart
(74) *Attorney, Agent, or Firm*—Baker & Daniels LLP

(57) ABSTRACT

A strap system is useable with an anesthesia/respiratory face mask having an axially extending gas port connector and a gasket member. The gas port connector has a first diameter, and the gasket member is engageable with and conformable to a face of a patient. The strap system includes a strap member having a first end portion, a second end portion and a middle portion, and a collar. The collar includes an axially extending portion having a second diameter. The strap system includes a strap having a first end portion, and a second end portion; the collar also includes a radially extending portion having at least a first and a second slot through which the first and second end portions, respectively of the strap can pass. The slots are sized for adjustably receiving and fixedly positioning the first and second end portions of the strap.

13 Claims, 8 Drawing Sheets

U.S. PATENT DOCUMENTS

| | | | |
|---|---|---|---|
| D285,733 S | 9/1986 | Cooper | |
| 4,635,628 A | 1/1987 | Hubbard et al. | |
| 4,657,010 A | 4/1987 | Wright | |
| 4,662,005 A | 5/1987 | Grier-Idris | |
| 4,705,033 A | 11/1987 | Halfpenny | |
| 4,765,325 A | 8/1988 | Crutchfield | |
| 4,796,621 A | 1/1989 | Barle et al. | |
| 4,802,473 A | 2/1989 | Hubbard et al. | |
| 4,807,619 A | 2/1989 | Dyrud et al. | |
| 4,910,806 A | 3/1990 | Baker et al. | |
| 4,920,580 A | 5/1990 | Liff | |
| 4,941,212 A | 7/1990 | Liff | |
| 4,941,470 A | 7/1990 | Hubbard et al. | |
| 5,107,547 A | 4/1992 | Scheu | |
| D326,933 S | 6/1992 | Feder | |
| 5,121,746 A | 6/1992 | Sikora | |
| 5,284,160 A | 2/1994 | Dryden | |
| D351,226 S | 10/1994 | Parvatharaj | |
| D355,715 S | 2/1995 | Hubbard et al. | |
| 5,404,873 A | 4/1995 | Leagre et al. | |
| 5,429,683 A | 7/1995 | Le Mitouard | |
| 5,462,050 A | 10/1995 | Dahlstrand | |
| 5,474,060 A | 12/1995 | Evans | |
| 5,503,147 A * | 4/1996 | Bertheau | 128/207.11 |
| 5,553,608 A | 9/1996 | Reese et al. | |
| 5,561,863 A | 10/1996 | Carlson, II | |
| D388,452 S | 12/1997 | Dreyfus | |
| 5,694,928 A | 12/1997 | Hoftman | |
| 5,699,791 A | 12/1997 | Sukiennik et al. | |
| 5,701,892 A | 12/1997 | Bledstein | |
| 5,738,094 A | 4/1998 | Hoftman | |
| 5,778,872 A | 7/1998 | Fukunaga et al. | |
| 5,819,731 A | 10/1998 | Dyrud et al. | |
| 5,921,239 A | 7/1999 | McCall et al. | |
| 5,975,079 A | 11/1999 | Hellings et al. | |
| 5,983,896 A | 11/1999 | Fukunaga et al. | |
| 6,003,511 A | 12/1999 | Fukunaga et al. | |
| 6,035,852 A | 3/2000 | Hoftman | |
| 6,062,222 A | 5/2000 | Lewis et al. | |
| 6,070,579 A * | 6/2000 | Bryant et al. | 128/207.11 |
| 6,095,143 A | 8/2000 | Dyrud et al. | |
| 6,116,903 A | 9/2000 | Zegarelli et al. | |
| 6,129,082 A | 10/2000 | Leagre | |
| 6,151,720 A * | 11/2000 | Chiang | 2/248 |
| 6,209,542 B1 | 4/2001 | Thornton | |
| 6,386,198 B1 | 5/2002 | Rugless | |
| 6,412,488 B1 | 7/2002 | Barnett et al. | |
| 6,439,231 B1 | 8/2002 | Fukunaga et al. | |
| 6,626,178 B2 | 9/2003 | Morgan et al. | |
| 6,644,314 B1 | 11/2003 | Elsberg | |
| 6,651,661 B2 | 11/2003 | Matioc | |
| 6,651,663 B2 * | 11/2003 | Barnett et al. | 128/207.13 |
| 6,718,982 B2 | 4/2004 | Smith et al. | |
| 6,736,139 B1 | 5/2004 | Wix | |
| 6,792,943 B2 | 9/2004 | Kumar et al. | |
| 6,889,390 B1 | 5/2005 | Morgan et al. | |
| 6,926,685 B1 | 8/2005 | Modglin | |
| 6,928,657 B2 | 8/2005 | Bell et al. | |
| 7,004,168 B2 | 2/2006 | Mace et al. | |
| 2003/0024533 A1 * | 2/2003 | Sniadach | 128/205.25 |
| 2003/0037788 A1 * | 2/2003 | Gallem et al. | 128/206.21 |
| 2003/0183232 A1 | 10/2003 | Fukunaga et al. | |
| 2006/0000476 A1 * | 1/2006 | Salem | 128/206.21 |
| 2009/0000624 A1 * | 1/2009 | Lee et al. | 128/207.11 |

OTHER PUBLICATIONS

Screen print from Narang Medical Ltd. (Www.narang.com) Apr. 2006.
Screen print from Anesthesia Accessories, MainLine Medical Inc. (www.mainlinemedical.com) Apr. 2006.
Screen print from Online Source for Anesthesia, Respiratory and Critical Care, Keomed Inc. (www.keomed.com) Apr. 2006.
Screen print from Vital Signs, Inc. (home.vital-signs.com) Apr. 2006.
Screen print from King Systems Corporation (Www.kingsystems.com) Apr. 2006.

* cited by examiner

FACE MASK STRAP SYSTEM

TECHNICAL FIELD OF THE INVENTION

The present invention relates to anesthesia and respiratory equipment, and more particularly, to a strap system for maintaining an anesthesia or respiratory face mask on the head of patient.

BACKGROUND OF INVENTION

A popular method for administering anesthesia and respiratory gases to a patient is by use of a face mask, which itself is fluidly coupled to other components of an anesthesia or respiratory system. The anesthesia or respiratory system typically includes a gas source, such as an oxygen canister for respiratory purposes, or anesthetic gas canister for the administration of anesthetic gases. A flow control device such as an anesthesia machine is disposed downstream of the gas storage canister for controlling the flow of gas to a patient. A breathing circuit fluidly couples the anesthesia/respiratory machine to the face mask, and includes a proximal end that is mechanically coupled to the anesthesia or respiratory machine, and a distal end that is mechanically coupled to the face mask.

Breathing circuits can be "one-way" circuits that only direct the anesthesia gas or respiratory gas to a patient; or alternately, can be dual circuits that include an inspiratory passage for conducting fresh and/or processed re-breathing gases from the anesthesia machine to the patient, and an expiratory gas passageway for conducting exhaled gases away from the patient.

Examples of breathing circuits, and the anesthesia machines to which they are attached are shown in Fukunaga et al, U.S. Pat. Nos. 6,439,231; 6,003,511; 5,983,896; 5,778,872 and 4,265,235. Additional examples of breathing circuits can be seen in Leagre and Burrow, U.S. Pat. No. 5,404,873; and U.S. Pat. Nos. 3,856,051; 3,556,097; 4,007,737; 4,188,946; 4,265,235; 4,463,755; 4,232,667; 4,596,246; 5,121,746; 5,284,160; 5,778,872; and 6,129,082. A good review of a variety of popular anesthesia circuit types can be found in Fukunaga et al., Published U.S. Patent Application No. US/2003/0183232 A1, that was published on 2 Oct. 2003.

As alluded to above, the face mask includes a connector that defines a gas port. The connector is typically coupled to the proximal end of a breathing circuit. The face mask is placed over the patient's face to cover the patient's nose and/or mouth, so that anesthesia gases may be delivered to the patient without intubation.

Many examples of anesthesia-type face masks exist. For example, various anesthesia face masks can be seen in the patent literature in Keener et al., U.S. Pat. No. 3,815,596; Dahlstrand, U.S. Pat. No. 5,462,050; Hoftman, U.S. Pat. No. 5,738,094; Hellings, U.S. Pat. No. 5,975,079; Hoftman, U.S. Pat. No. 6,035,852; Barnett et al., U.S. Pat. No. 6,412,488; Wix, U.S. Pat. No. 6,736,139; and Kumar, U.S. Pat. No. 6,792,943. Examples of breathing masks are also shown in many of the breathing circuit-related patents discussed.

In addition to the patent literature, several types of commercially available face masks exist. Among these masks are masks that are manufactured or distributed by companies such as Narang Medical, Ltd. (See www.narang.com); Mainline Medical (See www.mainlinemedical.com); Keomed, Inc. (See www.keomed.com); and VitalSigns, Inc. (See www.vital-signs.com). Additionally, the Assignee of the present invention, King Systems Corporation manufactures a wide variety of face masks, many of which can be seen at www.kingsystems.com.

The anesthesia face masks shown in prior art typically include a domed portion, having a generally cylindrical connector that defines a gas-receiving port. The connector is disposed at the top of the domed portion. The gas-receiving port is sized for receiving the distal end of a breathing circuit or respiratory tube. A torus-shaped air bladder is fixedly coupled to the lower perimetral edge of the face mask. The air bladder is designed for fitting against the face of the patient. The air bladder is formed from a thin flexible plastic material and is large enough, and inflated at a low enough pressure, to have the flexibility to enable the surface of the air bladder to conform to the patient's skin, to create a seal between the air bladder and the patient's skin. By creating this seal, the amount of anesthesia and other gases within the interior of the dome that escapes to atmosphere is reduced. This reduction of gas leakage helps to both ensure that the patient receives the full benefit of the anesthetic and respiratory gases that flow therein, and minimizes the contact between these respiratory and expiratory gases and persons working on the patient, such as doctors, nurses and the like.

Many air bladders include a valve that enables the practitioner to introduce air into, or remove air from the interior of the air bladder, and thereby adjust the air pressure therein, and the amount of conformability that the air bladder can exhibit, when placed adjacent to a patient's face.

One difficulty that is encountered with the use of a face mask is maintaining the face mask on the face of the patient during the procedure, and especially during a long term respiratory event. In order to maintain the face mask on a patient, the current procedure is to employ a ring and strap member configuration.

As best shown in Hellings, U.S. Pat. No. 5,975,079, and some of the web site excerpts discussed above, the ring member typically includes a ring having a central aperture that is sized to interiorly receive the generally cylindrical gas port connector, so that the ring can fit over the cylindrical gas port connector. The ring includes a plurality (usually 4 or 6) radially extending arms that are spaced in intervals around the circumference of the cylindrical part of the ring. An upwardly extending prong is formed on the distal (radially outward most) portion of each of the radially extending arms, and serves as a prong or stud member.

As best shown in FIG. 4 of Hellings '079 patent, and in FIG. 7 of the instant application, the strap typically comprises a heavy elasticized rubber or plastic strap having at least two series of apertures extending along the length of the strap. The middle portion of the strap is placed behind the head of the user, with the ends of the strap being placed adjacent to the dome of the mask. The upwardly extending stud-like prong members that are disposed on the distal ends of the ring are inserted through appropriately positioned apertures of the strap to attach the strap to the mask. Due to the elastic nature of the strap, one can effect a snug engagement of the mask to the user's head by stretching the strap slightly before inserting the prongs through the apertures of the strap, so that the compressive force exerted by the strap holds the mask snugly into engagement of the face of the patient.

Although this strap and ring method performs its intended function in a workman-like manner, room for improvement exists. In particular, the straps of the present kind have some less-than-desirable features that can be improved.

One less than desirable feature relates to the size and bulkiness of the strap. The size and bulkiness of the strap has the potential to create additional clutter around the patient's face that has the potential to impair a surgeons' or nurses' ability to work on the patient. Another undesirable attribute of the strap and ring arrangement used currently is that the straps and ring are relatively expensive to manufacture and purchase, when compared to the strap of the present invention that will be discussed below.

Another less than desirable feature of the strap and ring arrangement of the prior art can best be understood by viewing the series of aperatures in the strap, into which the prong can be inserted. These apertures provide a limited range of incremental adjustability of the size of the strap. Although the plurality of apertures enable the user to effect the size of the strap to a number of different sizes generally equal to the number of apertures in any particular series, the number of incremental adjustments is limited by the number of apertures, Further, the size of the particular increments in which the strap can be adjusted is also limited by the distance between adjacent apertures. This incremental adjustability of the aperture and prong type straps of the prior art, could be improved if a system were devised that would permit infinite adjustability, or at least an adjustability wherein the adjustments could be made in increments smaller than the increments provided by the strap of the prior art.

One object of the present invention is to provide a ring and strap system for maintaining an anesthesia face mask on the head of the user, that is less expensive, and adjustable in smaller increments than the strap and ring system of the prior art discussed above.

SUMMARY OF THE INVENTION

In accordance with the present invention, a strap system is provided for use with an anesthesia/respiratory face mask having an axially extending gas port connector. The gas port connector has a first diameter, and a gasket member engageable with and conformable to a face of a patient. The strap system comprises a strap member having a first end portion, a second end portion and a middle portion, and a collar. The collar includes an axially extending portion having a second diameter. The first diameter and second diameter are sized, relative to each other to define a gap between the axially extending portion of the collar and the axially extending portion of gas port connector through which the first and second end portions of the strap pass. The gap is sized for snugly receiving the strap between the collar and the gas port connector.

In a preferred embodiment, the axially extending portion of the collar includes at least two slots for receiving the strap member that can be extended in the gap, and then through the slot members to better fix the position of the strap in the gap.

Additionally, the strap member should preferably have a width substantially greater than its thickness, and may have a shoe strong-like size and shape. The strap should also have a rest length, and be comprised of an elastic material that has sufficient elasticity to enable the length of the strap to be increased by at least 10% from its rest length.

In accordance with an alternate embodiment of the present invention, strap system is provided for use with an anesthesia/respiratory face mask having an axially extending gas port connector and a gasket member engagable with and conformable to a face of a patient. The strap system comprises a strap member having a first end portion, a second end portion and a middle portion. A collar includes a radially extending portion and has at least a first and a second slot through which the first and second end portions, respectively of the strap can pass. The slots are sized for adjustably receiving and fixedly positioning the first and second end portions of the strap.

Preferably, the radially extending portion includes first and second tab portions, wherein the two slots are disposed. The axially extending portion of the collar member is preferably sized for receiving the axially extending gas port connector, and the radially extending portion of the collar is placeable against a radially extending portion of the face mask.

One feature of the present invention is that it includes a relatively small and inexpensive elastic strap that is sized to fit between the gap created by the axially extending portion of the collar and the gas port connector. This feature has the advantage of providing a secure head strap system that is substantially less expensive to manufacture, and less bulky to use than prior art strap systems. The strap system of the present invention reduces the costs both of producing the strap, and of producing the collar. The cost of producing the strap is reduced as a smaller, less expensive strap is used in place of the bulkier, more expensive prior art strap. Additionally, the price of the collar is reduced, as the collar need not be manufactured to include the radially extending arms and upraised prongs of the prior art system.

Another feature of one embodiment is that the engagement between the strap and collar results from a frictional engagement between a strap, and a gap between the collar and the gas connector port (the first embodiment), or by the frictional engagement of the strap in a slot contained within the collar (in the second embodiment). This feature has the advantage of providing a strap system wherein the effective length of the strap is virtually infinitely adjustable. This feature represents an improvement over the limited, incremental adjustments possible with the prong and aperture system of the known prior art.

One feature of a most preferred embodiment of the present invention, is that it includes a combination of radial arms; strap-engaging slots disposed in the radially extending portion of the collar; and slots disposed in the axially extending portion of the collar. This most preferred embodiment has the advantage of encompassing, in one device, three different vehicles for engaging a strap to a face mask. Although, for the reasons set forth above, the Applicants believe that the thin, shoe string-like face mask that is engagable with either the slots on the radially extending portion of the collar, or otherwise disposed between the collar and the face mask gas port have a significant advantages over the use of the relatively thicker, aperture-containing strap that hooks onto the radially extending arms, it will be appreciated that certain practitioners will prefer to use the more classic aperture-containing strap.

This divergence in preference between various practitioners can create problems for a hospital purchasing manager, as it may force that purchasing manager to purchase different types of collars to accommodate different preferences. By creating a collar that will accommodate both the traditional, aperture-containing wide strap, and the Applicants' new shoe string-like strap, the purchasing manager's job is made more simple, as she is relieved from the burden of carrying two different parts in inventory, but instead need purchase only a single part that accommodates both different type straps.

These and other features of the present invention will become apparent to those skilled in the art, upon a review of the drawings and detailed description set forth below, that describes the best mode of practicing the present invention perceived presently by the applicants.

DETAILED DESCRIPTION

Figure 6:
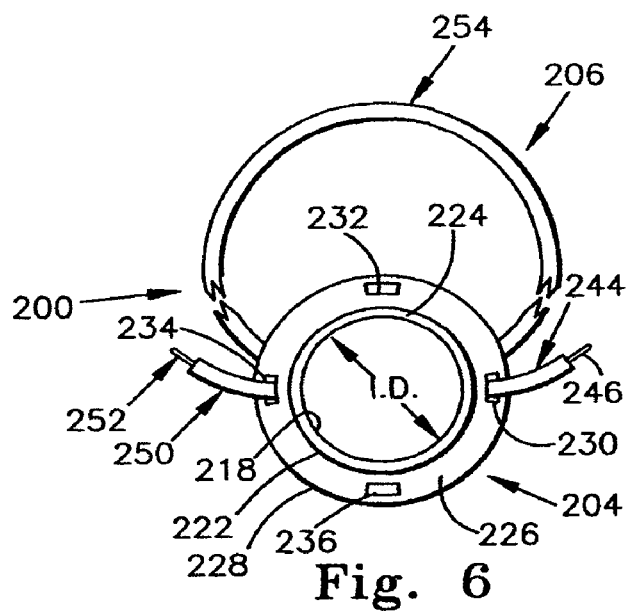
FIG. 6 is a top view of the first alternate embodiment collar member, showing the collar assembled with a strap.
Figure 5:
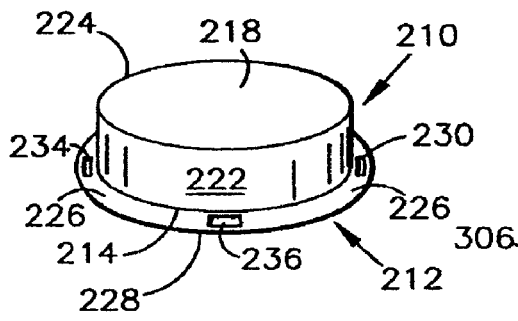
FIG. 5 is a side view of a first alternate embodiment collar member.
Figure 10:
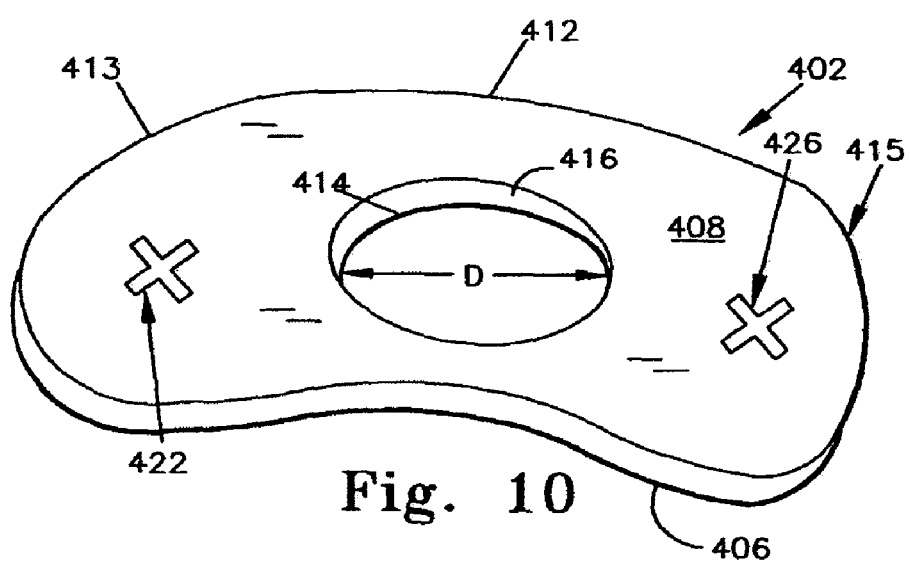
FIG. 10 is a top view of the collar of the third embodiment.
Figure 11:
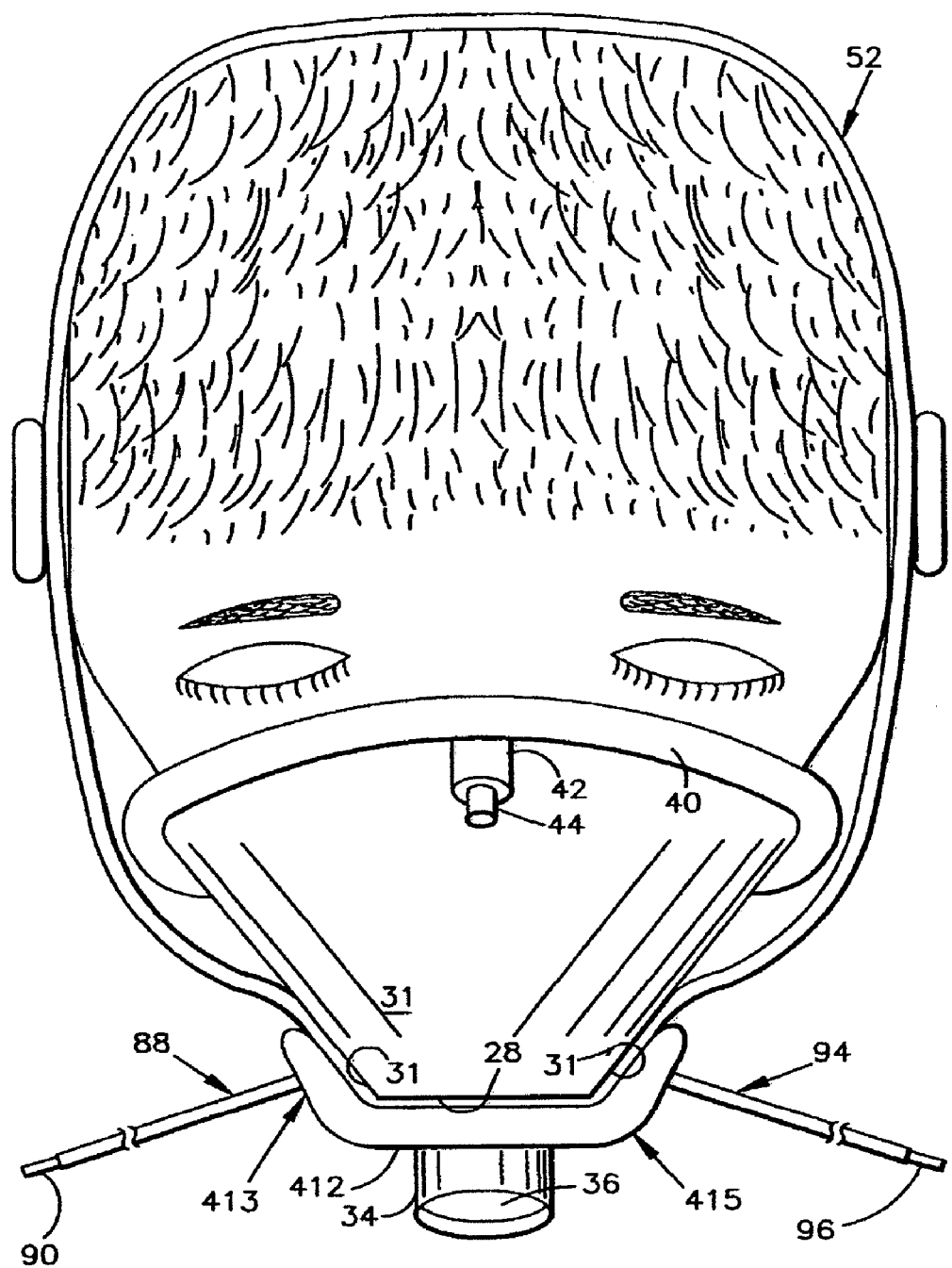
FIG. 11 is a top view of the third embodiment strap system and face mask on the head of a patient.
Figure 12:
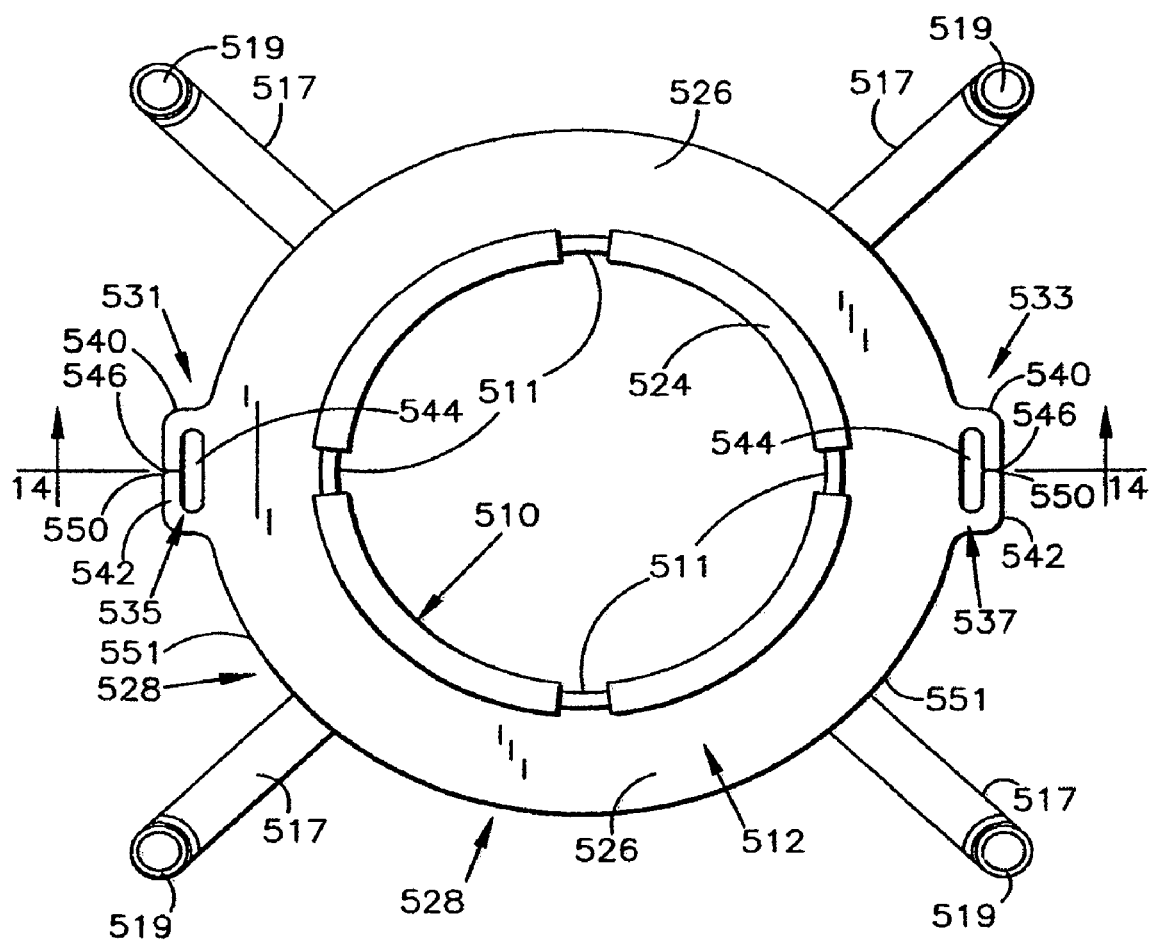
FIG. 12 is a top view of a fourth embodiment collar member.
Figure 13:
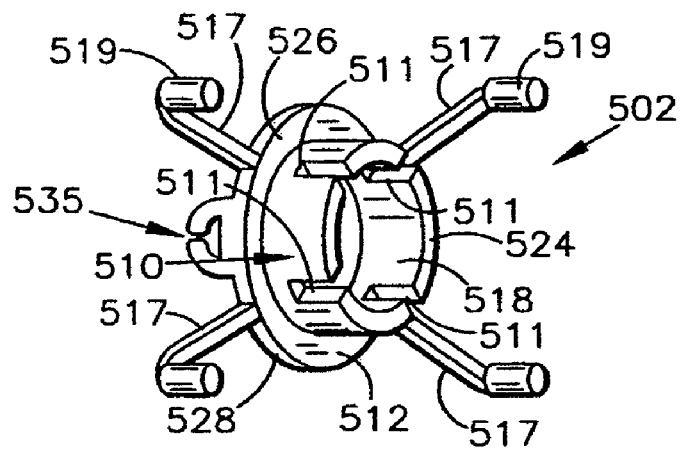
FIG. 13 is a perspective view of the fourth embodiment collar member.
Figure 14:
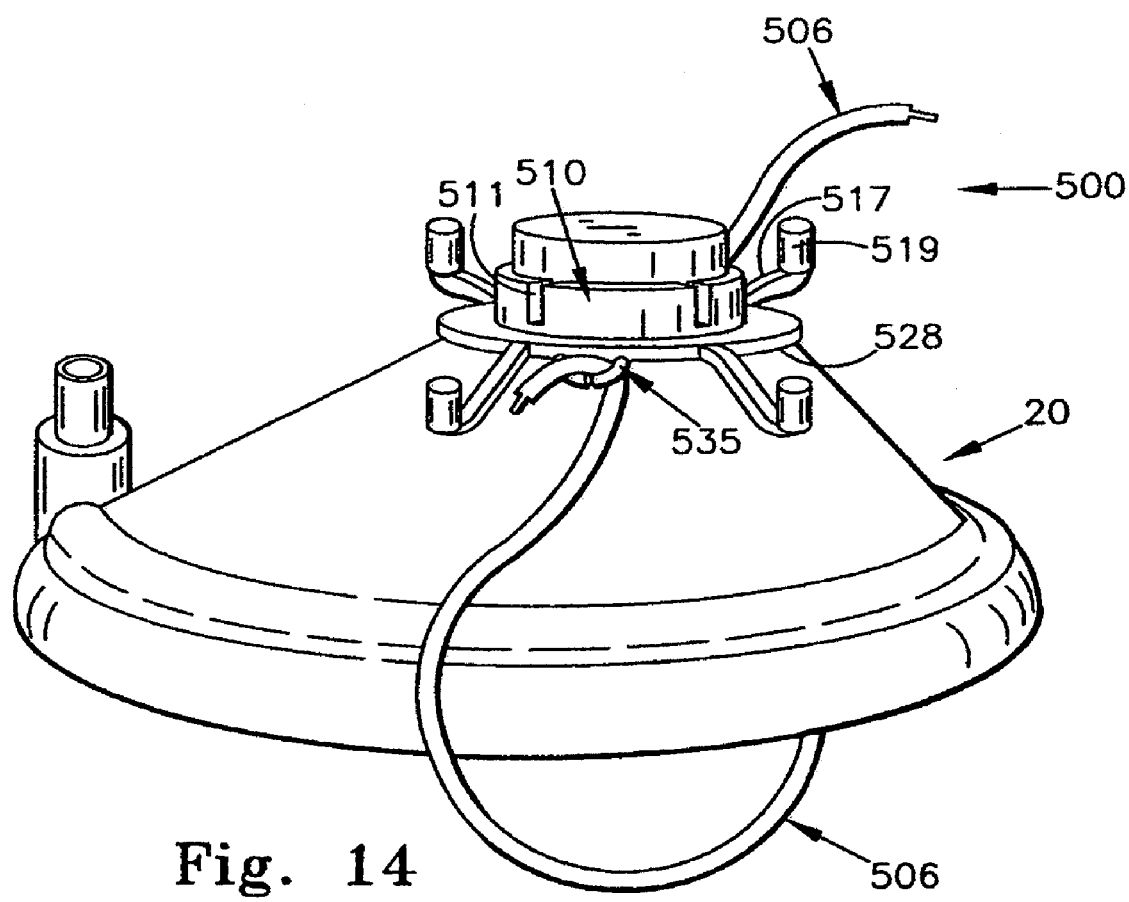
FIG. 14 is a side view of the fourth embodiment collar member, as shown being attached to a face mask and strap.

The first embodiment of the face mask strap system 10 of the present invention is shown in FIGS. 1-4, and a second embodiment 200 is shown in FIGS. 5-6. A third embodiment 400 is shown in FIGS. 8-11, and a fourth embodiment is shown in FIGS. 12-14. However, before discussing the face mask strap systems 10, 200, 400 of the present invention, it is first helpful to understand the prior art face mask strap system 300, that is shown in FIG. 7.

Figure 7:
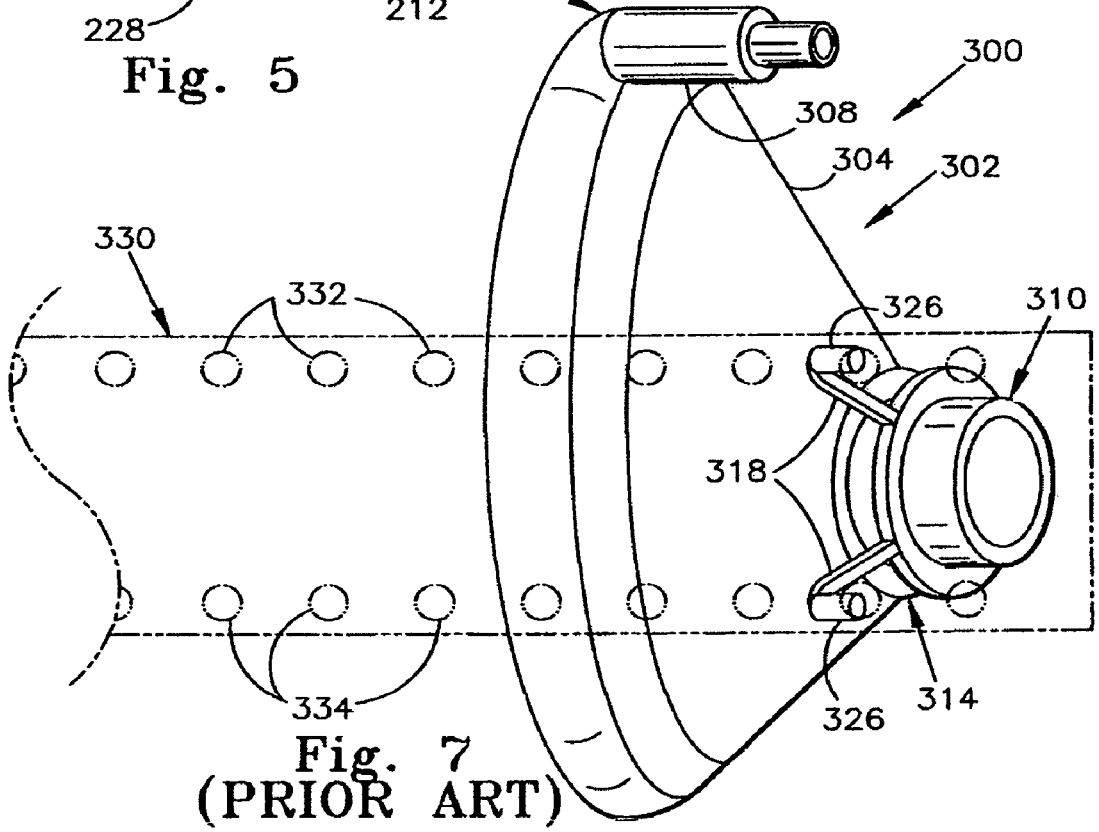
FIG. 7 is a side view of a prior art face mask ring and strap system.
Figure 8:
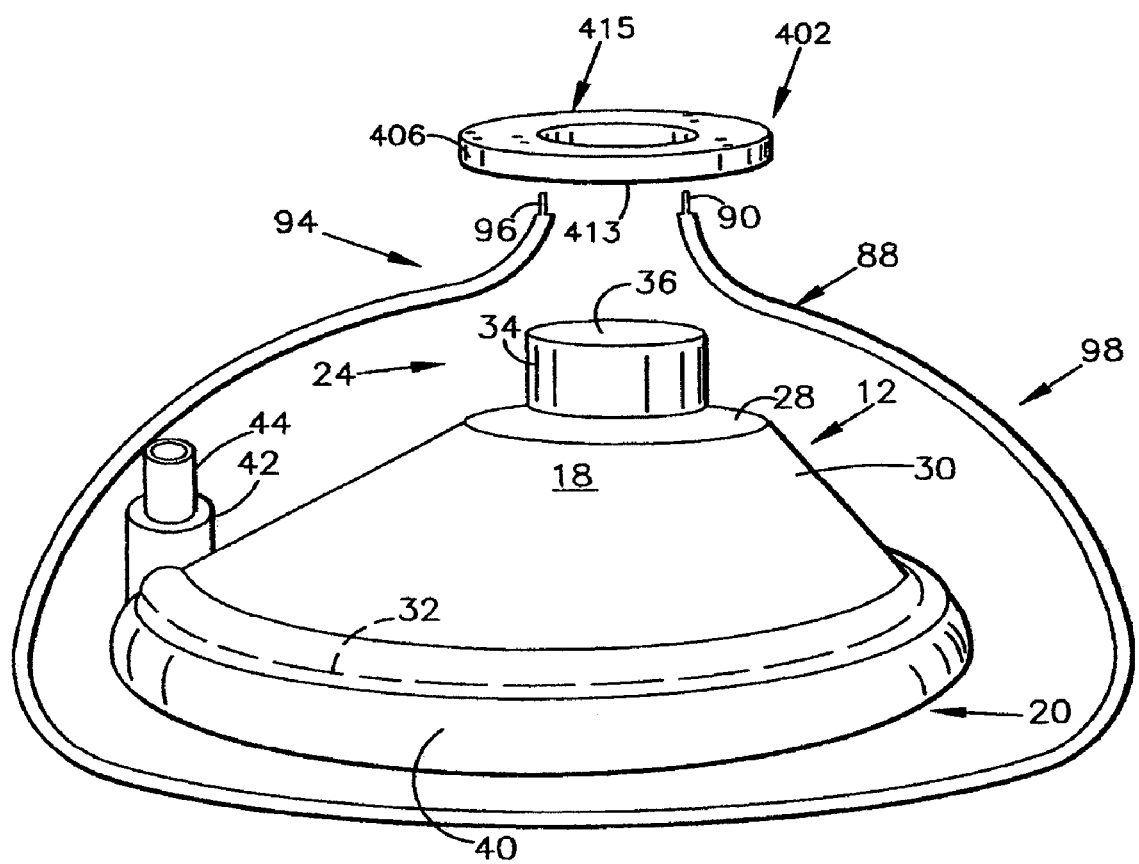
FIG. 8 is an exploded side view of a third embodiment of the present invention.

Turning now to FIG. 7, a prior art face mask strap system 300 is shown for providing a means for holding an anesthesia/respiratory face mask 302 on to the head of a patient. The anesthesia/respiratory face mask 302 includes a generally clear dome portion, that is generally elliptically frusto-conical in configuration. An air bladder 306 extends perimetrally around the lower edge of the dome portion 304, and includes an air valve 308 for enabling the user to either introduce or remove air from the air bladder 306 to adjust the air pressure within the air bladder 306, and thereby adjust the conformability of the air bladder 308 to the face of the patient on which it is used. A gas port connector 310 is disposed at the top of the dome portion.

A separately formed collar 314 has a radially inwardly facing interior surface that defines an aperture, for receiving the gas port connector 310, to permit the collar 314 to fit over the gas port connector 310. The collar 314 also includes four radially extending arms 318 that are disposed at even intervals around the radial periphery of the collar 314. Although the collar 314 includes four radially extending arms, only two are shown in the drawings, with the other two being hidden (in FIG. 7) by the face mask.

Each of the radially extending arms 318 includes an upstanding prong 326 that is disposed at the distal end of the respective radially extending arms 318. As alluded to above, face masks 300 and collars, 314 such as those shown in FIG. 7 are known in the prior art, and are produced by a variety of manufacturers. A generally wide, somewhat elastic strap member 330 includes a first linear array of spaced apertures 332, and a second linear array of spaced apertures 334. The aperture arrays are separated from each other by a distance sufficient to permit them to be received by prongs 326 that are disposed on an adjacent radially extending arms 318.

As alluded to in the Background portion of the instant application, straps, such as strap 330 were derived originally from the straps used on aviation face masks, of the type that a military pilot may wear. When used in such aeronautical applications, the heavy, relatively non-elastic strap performs quite well in holding the face mask onto the face of the pilot, especially in situations where the pilot's head is subject to large amounts of rapid movement, as one might expect to occur during a combat flight.

However, when used in an anesthesia situation, the straps, shown in FIG. 7 have certain draw-backs. For example, the straps are only capable of incremental adjustment, are heavy and are cumbersome. These disadvantages are also discussed in more detail above in the Background portion.

Although the heavy-duty nature of straps, such as strap 330 are warranted in aeronautical applications, they constitute overkill in an anesthesia/respiratory environment, wherein the user's head is not likely to undergo the amount and degree of movement that one might expect while piloting an airplane. As such, the bulkiness and extra expense that accompany such straps provide disadvantages, without providing benefits of the type that are usually needed within an operating room or respiratory care environment.

Although the trade off between the incremental only adjustability of a face mask, and the resultant strength of the strap may be a viable trade off in an aeronautical environment, it is not necessarily a viable trade off within an anesthesia or respiratory environment. In such an operating room or respiratory therapy environment, it would be preferred to be able to attain essentially infinite adjustability, even if such infinite adjustability includes the cost of being a less secure method of holding the face mask onto a patient's head.

The strap system 10, 200 of the present invention provides an inventive device for overcoming many of the drawbacks of such prior art strap systems 300.

A first embodiment strap system 10 of the present invention is shown in FIGS. 1-4. The strap system 10 is designed for use with an anesthesia/respiratory face mask 12, that is generally similar to face mask 302 shown in FIG. 7. The face mask 12 includes an elongated, generally elliptical frusto-conically shaped transparent dome portion 16, that defines the interior space 18 between the dome portion 16 and the face of the patient. The face mask 12 includes a gasket, such as a Torus-shaped air bladder 20 that is fixedly coupled to the lower edge of the dome portion 16, and a gas port connector 24 that extends axially outwardly, and is disposed adjacent to the top of the dome portion 16. Preferably, the gas port connector 24 is unitarily formed with the dome portion 16. In lieu of an air bladder, the gasket can be made of a soft, highly pliable plastic.

The dome portion 16 includes a radially extending top shelf 28, and a frusto conical, annular wall 30. The radially extending top shelf 28 joins the frusto-conical wall 30 with the gas port connector 24. A perimetral lower lip 32 (shown in phantom) extends around a lower edge of the dome portion 16, and provides a surface to which the air bladder 20 may be fixedly and sealingly coupled, to join the air bladder 20 to the dome portion 16.

The gas port connector 24 extends axially, and includes a generally cylindrical wall 34, that defines an interior gas port 36, that permits fluid communication between the interior space 18, and the environment. In practice, the gas port connector 24 is coupled to the distal end of the breathing or respiratory circuit, so that the gas port 36 may transfer gasses between the interior space 18, and the interior air space of the breathing circuit (not shown).

The air bladder 20 includes a generally hollow interior 40 that can be filled with a fluid, such as air. Preferably, the air within the air bladder 20 is placed at a low enough pressure, to permit the relatively thin plastic walls of the air bladder 20 to conform to the skin of a patient, to provide a generally air-tight seal between the interior space 18, and the ambient atmosphere outside the dome 16 and air bladder 20. An air valve 42 having an inlet port 44 is provided for permitting the user to adjust the amount of air within the hollow interior 40, to thereby adjust the conformability of the air bladder 20 to the face of the patient.

The strap system 10 of the present invention includes two primary components, a collar 50 and a strap 52. The collar 50 is preferably unitarily formed from a transparent plastic material, and includes a generally cylindrical axially extending portion 56 and a radially extending flange type portion 60 that is disposed in a plane generally perpendicular to the axis of the generally cylindrical axially extending portion 56. The axially extending portion 56, and the radially extending portion 60 are joined at the base 61.

The generally cylindrical axially extending portion 56 includes a radially inwardly facing surface 62 that has an inner diameter, ID of about 1.04 inches, (26.5 mm.). This particular ID is chosen so that the central aperture defined by the radially inwardly facing surface 62 can receive the radially outwardly facing surface of the gas port connector 24.

Preferably, the difference between the outer diameter of the wall 34, and the inner diameter ID of the collar 56 creates a gap of between about 1.4 and 2.0 mm, and preferably of about 1.6 mm, which, as will be explained in more detail later, is sized for enabling the first and second end portions 88, 94 of the strap 52 to fit between the radially outwardly facing surface of the wall 34 and the radially inwardly facing surface 62 of the axially extending portion 56 of the collar 50, so that the strap 52 is snugly engaged between the collar 56 and the wall 34. This snug fit should be such that the strap 52 will normally be held in a fixed position between the gas port connector 24, and the axially extending portion 56. However, the gap should be sufficiently great so that the end portions 88, 94 of the strap 52 can be pulled linearly (in a direction parallel to the long axis of the strap 52) in the gap to either tighten or loosen the strap 52 around the user's head, by the user tugging or pulling on the strap 52.

Figure 2:
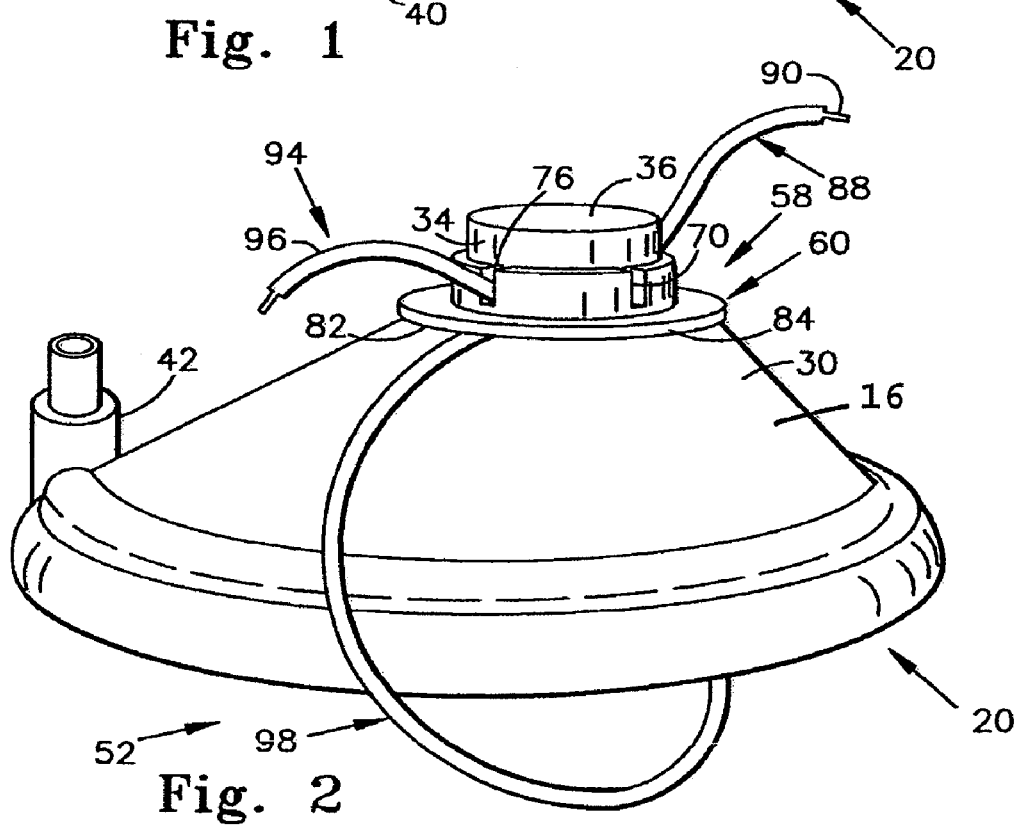
FIG. 2 is an assembled side view of the present invention.

The axially extending portion 56 also includes a radially outwardly facing surface 66, and an upper edge surface 68. Four axially extending slots, including first slot 70, second slot 72, third slot 74 and fourth slot 76 are formed in the axially extending portion 56. The slots 70-76 are sized for enabling the first and second end portions 88, 94 of the strap 52 to pass therethrough, such as is best illustrated in FIG. 2. Preferably, the slots 70-76 each have a length of approximately 0.27 in, (7.0 mm.), and a width of approximately 0.06 in. (1.6 mm.). The positioning of the slots 70-76 helps to facilitate locking the strap member 52 in a fixed position on the collar 50, when the strap end portions 88, 94 are passed through appropriate slots, such as is shown in FIG. 2.

It has been found by the applicant that the force required to move the first and second end portions 88, 94 within the gap between the radially inwardly facing surface 62, and the gas port connector 24, is significantly greater when the first and second end portions are engaged within slots, such as slots 72, 76 as shown in FIG. 2. As a corollary, the sizing of the gap created between the radially inwardly facing surface 62 of the collar 50 and the radially outwardly facing surface of the wall 34, when combined with the passage of the first and second end portions 88, 94 within the slots 70, 76, tends to fix the linear position of the strap 52 within the gap over a range of forces that are typically exerted on the strap, during the strap system 10 and face mask's 12 engagement with the head of the user during a surgical or respiratory therapy procedure. If it is desired to adjust the length of the strap 52 during a procedure, the end portions 88, 94 of the strap 52 must generally be removed from their engagement with the slots 70-76 before such linear adjustment can be practically effected by the medical personnel attending to the patient.

The radially extending portion 60 of the collar 50 includes an axially outwardly facing surface 80, and an axially inwardly facing surface 82. When the collar 50 is placed onto the face mask 12, a radially inwardly facing surface 82 engages the shelf-like radially extending surface 28 of the face mask, that provides a rest for the collar 50. The radially extending portion 60 extends approximately 2.85 mm. outwardly from the base 61, and terminates at an outer edge 84.

The strap 52 is preferably configured to be similar to a shoe string in length, width and thickness. However, the strap 52 is preferably comprised of an elastic material, that has sufficient elasticity so that, for example, it will have a rest length of approximately 20.5 in. (520.7 mm.); and a fully stretched length of 48 in. (1219.2 mm.), so that its expanded length is approximately 134 percent greater than its rest length.

The strap 52 includes a first end portion 88 that terminates at a first wrapped end 90; a second end portion 94 that terminates at a second wrapped end 96; and a middle portion 98 extending between first and second end portions 88, 94, respectively. The first and second wrapped ends 90, 94 are similar to the wrapped ends of a shoe string, wherein the generally, flat, rectangular sheet like elastic cloth material from which the strap 52 is made is wrapped within a piece of plastic, or cellophane tape to form a generally rigid, cylindrical end. This wrapping both facilitates the threading of the strap 52, and also prolongs the useful life of the strap by helping to prevent the fraying of the ends of the strap 52.

To operate the device 10, the first and second end portions 88, 94 are inserted into the central aperture of the collar 50 that is defined by the radially inwardly facing surface 62 of the axially extending portion 56 of the collar 50. The first and second end portions 88, 94 are pulled through the aperture, until such point as a few inches or so of each end portion 88, 94, extend through the aperture. The collar 50 is then placed over the gas port connector 34, so that the first and second end portions 88, 94 are captured in the gap between radially inwardly facing surface 62 of the collar 50, and the gas port connector 34.

Figure 3:
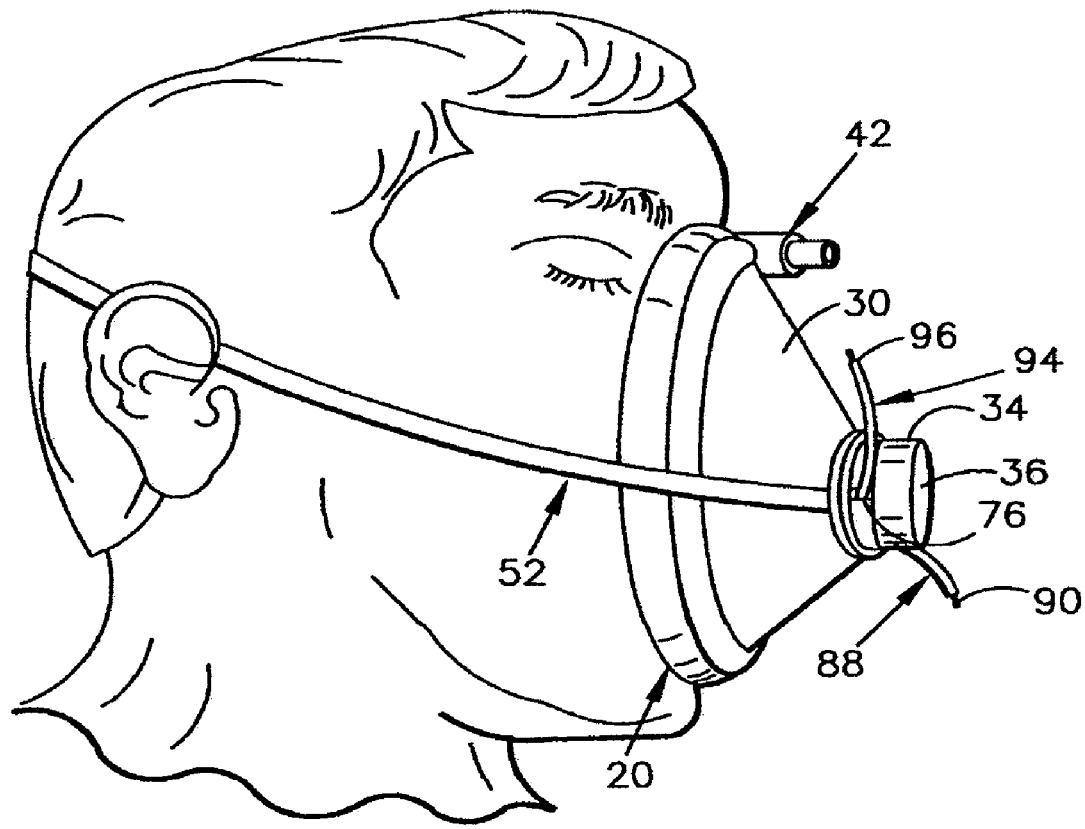
FIG. 3 is a side view of the strap system and face mask on the head of a patient.
Figure 4:
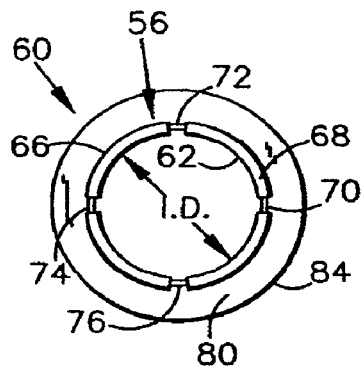
FIG. 4 is a top view of the collar member.

As best shown in FIG. 3, the face mask and strap arrangement is placed over the user's face so that the strap extends over the patient's ears, and around the back of his head. The air pressure within the air bladder 20 adjusted so that the air bladder 20 forms a good seal against the skin of the patient. The first and second end portions 88, 94 are then pulled outwardly, through the gap between the collar 50 and the gas port connector, to a point wherein the strap 52 is taut, so that a secure engagement of the face mask 12 to the head of the user is created. However, the strap 52 should not be pulled so tightly so as to cause any significant pain or discomfort to the user.

Once the strap 52 is properly adjusted, each of the first and second end portions 88, 94 are pulled through one of the four slots, 70-76. Because of the positioning of the strap, it is typical that the two end portions 88, 94 will be pulled through a pair of slots (e.g. 72, 76 of FIG. 2) that are disposed 180 degrees apart.

Once the straps are placed through the slots, the additional frictional engagement provided by the slots will serve to essentially lock the strap 52 in place, so that further linear movement of the strap 52 within the gap between the collar 50 and gas port connector 34 is effectively precluded, except upon the application of a very large and significant amount of force, in an amount typically greater than would be exerted on the strap by the patient moving his head around.

If the strap 52 needs further adjustments, such adjustments can be made by disengaging one or both of the end portions 88, 94 from their respective slots, and pulling on the strap 52, in the appropriate direction, to either loosen or tighten the strap. Because no fixed or incremental attachment points exist, (such as in the prior art shown at FIG. 7), the effective length of the strap 52 can be infinitely adjusted, until such point as the strap is adjusted appropriately for the particular user.

An alternate embodiment strap system 200 is shown in FIGS. 5 and 6. Although a face mask is not shown in FIG. 5 or 6, it will be understood that the strap system 200 is designed to be used with a face mask similar to face mask 12, shown in FIGS. 1-3.

The second embodiment strap system 200 includes a collar 204 and a strap 206. The collar 204 includes a generally cylindrical axially extending portion that is sized generally similarly to the axially extending portion 56 of the first embodiment, except that it does not include slots, such as slots 70-76. The collar 204 also includes a radially extending portion 212 that is sized and positioned generally similarly to its counterpart in the first embodiment, and is joined to the cylindrical portion at a base line 210.

The generally cylindrical axially extending portion 210 includes a radially inwardly facing surface 218 that defines an inner diameter ID that is preferably generally similar to the inner diameter ID of the first embodiment. However, the inner diameter ID defined by radially inwardly facing surface 218 may be slightly smaller, to grip the gas port connector (not shown) more snugly, as there is less need to create a gap between the radially inwardly facing surface 218 and the gas port connector, through which the strap 206 can pass, as the alternate embodiment strap system 210 does not require the passage of strap into this gap.

The axially extending portion 210 also includes a radially outwardly facing surface, that terminates at an upper edge 224. The radially extending portion 212 includes an axially outwardly facing surface 226, and an axially inwardly facing surface 227, and terminates at a radially outwardly disposed outer edge 228.

The radially outwardly extending portion 212 includes four slotted apertures, that are preferably separated by approximately 90 degrees. The four slotted apertures include first slotted aperture 230, second slotted aperture 232, third slotted aperture 234, and fourth slotted aperture 236. Each of the slotted aperture may either be rectangularly linear, or arcuate, and are preferably sized to snugly receive the strap member 206.

This particular dimension was chosen, both because there is sufficient room to make a slotted aperture of this size on the collar member, and also because it accommodates a strap member 206 sized similarly to strap 52. However, the slots could be smaller, if a smaller strap were used, or alternately, larger, if a larger strap is desired.

When sizing the strap member 206 and slotted apertures 230-236, the slotted apertures should be designed to be large enough to enable the strap member 206 to pass therethrough, without undue frictional resistance, but to still provide enough frictional resistance to prevent the strap member from being pulled out of the apertures, or adjusting its linear position within the apertures when the strap system 200 and face mask are attached to the head of the user.

The strap member 242 is generally similar, if not identical to strap member 52, in size, shape, configuration, and materials. Strap member 242 includes a first end portion 244 having a wrapped end 246; a second end portion 250, having a second wrapped end 252; and a middle portion 254 that extends there between.

To operate the strap system of this alternate embodiment, the first and second end portions 244, 250 are each pulled through their respective aperture, such as apertures 230, 234. Preferably, two apertures, (e.g. 230, 234) are chosen that are disposed 180 degrees from each other.

After the end portions 244, 250 are pulled through their respective apertures 230, 234, the central aperture of the collar 204 is fitted over a gas connector (e.g. 34) of the face mask 12. The position of the end portions 244, 250 of the strap member are then linearly adjusted to their appropriate length after the strap system 206 and face mask are placed onto the head of the user. As with the first embodiment, the strap member should be adjusted to be tight enough to still hold the face mask 12 snugly onto the face of the user, without being so snug so as to cause any pain or undue discomfort to the user.

A third embodiment strap system 400 is shown in FIGS. 8-11. Strap system 400 includes a collar 402 that is attached to a face mask 12 with a strap 52.

Face mask 12 and strap 52 are generally similar to the face mask 12 and strap 52 that are used in connection with the other embodiments. As such, numbers will be used for the face mask 12 and strap 52 in FIGS. 8-11 that are identical to those used in connection with the other embodiments.

The third embodiment collar 402 differs from collars 50, 204 that are used in connection with the first two embodiments, shown in FIGS. 1-6. Collar 402 is generally sheet-like and planar in configuration, and is made from a soft, pliable, somewhat elastic sheet of plastic that has sufficient flexibility to bend under the exertion of force. Preferably, the collar 402 is made from a clear vinyl or PVC flexible sheet, that has a thickness of about 0.07 inches.

The collar 402, has a generally planar upper surface 406, and a generally planar lower surface 410. As best shown in FIG. 10, the collar 402 includes a central portion 412 that includes a central aperture 414; a first side portion 413 that includes a first X-shaped strap-receiving slot 422; and a second side portion 415 that includes a second X-shaped strap-receiving slot 426.

Figure 9:
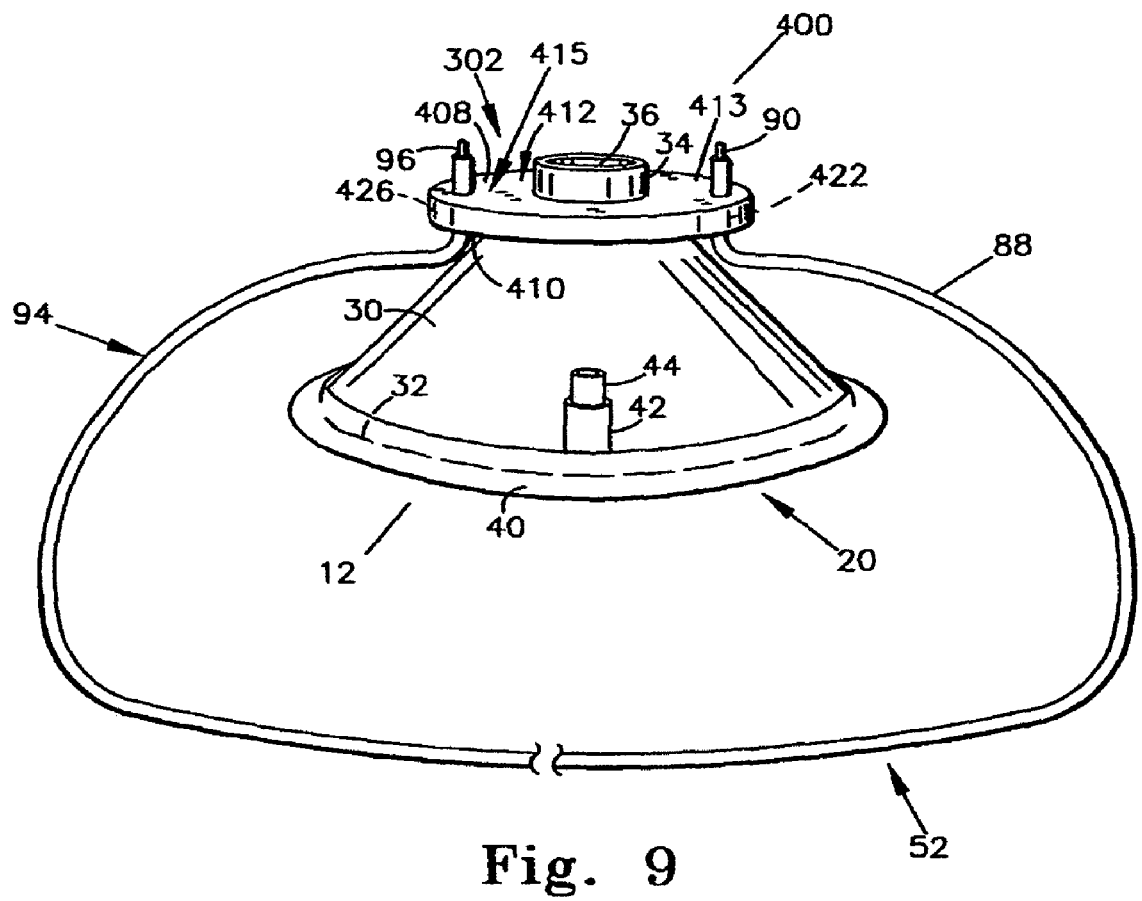
FIG. 9 is an assembled side view of the third embodiment.

The central aperture 414 is disposed generally at the center of the collar 402, and includes a radially inwardly facing surface 416 that defines a diameter D. As is shown in FIGS. 9 and 11, the central aperture is sized for receiving the gas connector port 34. The diameter D should be sized to snuggly engage the radially outwardly facing surface of the gas receiving port 34. Because of the generally flexible and somewhat elastic nature of the plastic material from which the collar 402 is made, the diameter D can be slightly smaller, identical, or just slightly larger than the outer diameter of the gas connector port 34. As a standard connection fitting for a gas connector port 34 is generally about 25.5 mm, the preferred diameter D of the central aperture 414 is preferably between about 24 and 27 mm.

The elasticity of the material from which the collar 402 is made enables the user to expand the diameter D of the central aperture 414, to enable the central aperture 414 to receive the gas connector port 34, even though the diameter D may be slightly smaller than the outer diameter of the gas connector port 34.

Alternately, the diameter D of the central aperture 414 can be sized to be slightly greater than the diameter of the connector port 34, to permit the collar 402 to slip over the gas receiving port 34 more easily. The relationship between the collar 402 and gas connector port 404 should be a snug relationship, with some frictional engagement between the radially inwardly facing surface 416 of the collar 402 and the radially outwardly facing surface of the gas connector port 34. This frictional engagement helps to maintain the collar 402 onto the gas connector port 34, by keeping it from falling off if the collar 402 containing mask 12 is moved around.

The first and second X-shaped slots 406, 422 are provided for receiving the first and second end portions 88, 94 of the strap 52. Because of the elasticity of the material from which the collar 402 is made, the first and second X-shaped slots 422, 426, can be manufactured as X-shaped slits, with little to no material being removed from between opposed sides of the X. As the strap is pulled through the slits, the four "corner members" that define the X will be able to bend to allow sufficient clearance for the strap ends 88, 94 to be pulled through the slit. Upon release of the strap, the memory of the collar 402 material is sufficiently great so that the sides of the "corner members" that define the X will frictionally engage the strap 52 to hold it in place. Alternately, the X-shaped slot members 422, 426 can be designed to have some space in between adjacent sides, such as is shown in FIG. 10.

Through the arrangements described above, the infinite adjustability of the other embodiments is preserved, as the medical practioner, to tighten the face on to the patient can pull the straps in infinite increments through the X-shaped slots 422, 426, until such point as the mask 12 fits snuggly.

Turning now to FIG. 11, the deformability of the collar 402 is demonstrated.

When the first end portions 88, 94 of the straps 12 are inserted through the slots 422, 426 and pulled snuggly to tighten the mask 12 on the face of the user, it will be noted that the first end portion 413 and second end portion 415 of the otherwise planar collar 402 deform. When so deformed, the middle portion 412 is disposed in a plane that is generally parallel with the plane of the top shelf 28 of the mask 12. By contrast, the first and second end portions 413, 415 are bent, so that they become disposed in positions that are generally parallel to the arcuate plane of the outer surface 31 of the frusto-conical portion of the face mask 12.

As the collar 402 is formed as a generally unitary member, there is no definite line of demarcation between the middle portion 412 and the first and second end portions 413, 415. Rather, for the sake of clarity in this description, the middle portion 412 can be envisioned as that portion of the collar 402 that generally overlays the axially outwardly facing top shelf 28 of the face mask 12. The first 413 and second 415 end portions are those portions of the collar 402, that are disposed on either side of the middle portion 412 and overlay the frusto-conical portion of the mask 12.

When the first and second end portions 88, 94 of the straps are pulled through the first and second X-shaped slots 422, 426 respectively, the first and second end portions 413, 415 are those portions that become disposed in a plane that is disposed at an oblique angle to the plane in which the middle portion 412 is disposed. As discussed earlier, the plane in which the first and second end portions 413, 415 becomes disposed after deformation is generally parallel or tangential to the arcuate plane of the radially outwardly facing surface 31 of the frusto-conical portion of the face mask 12.

It will be noted that some space exists between the first and second end portions 413, 415; and the outwardly facing surface 31, to permit the strap end portions 88, 94 to pass between the outer surface 31 of the face mask 12 and the collar 402.

One of the benefits obtained through the use of the flexible collar 402, is that it is less expensive to manufacture than either of the collar 56, 210 of the first and second embodiments.

One vehicle for saving money is that the collar 402 can be manufactured through a stamping process. In a stamping process, a sheet of material can be drawn through a stamping machine wherein the aperture for the central aperture 412, and X-shaped slots, for the first and second strap receiving slots 422, 426 can be punched, or cut out.

As such stamping or cutting tools are usually less expensive to purchase than injection molding type tooling, the use of such stamping or cutting technology, rather than injection molding technology as is required with the first and second embodiments (along with the prior art) will save the manufacturer substantial sums in tooling. However, cost savings can also be achieved even if an injection molding technique is used, as it should be less expensive to manufacture a relatively simple tool to manufacture the relatively elegant collar 402, when compared to the first and second embodiments, and especially the prior art.

Figure 1:
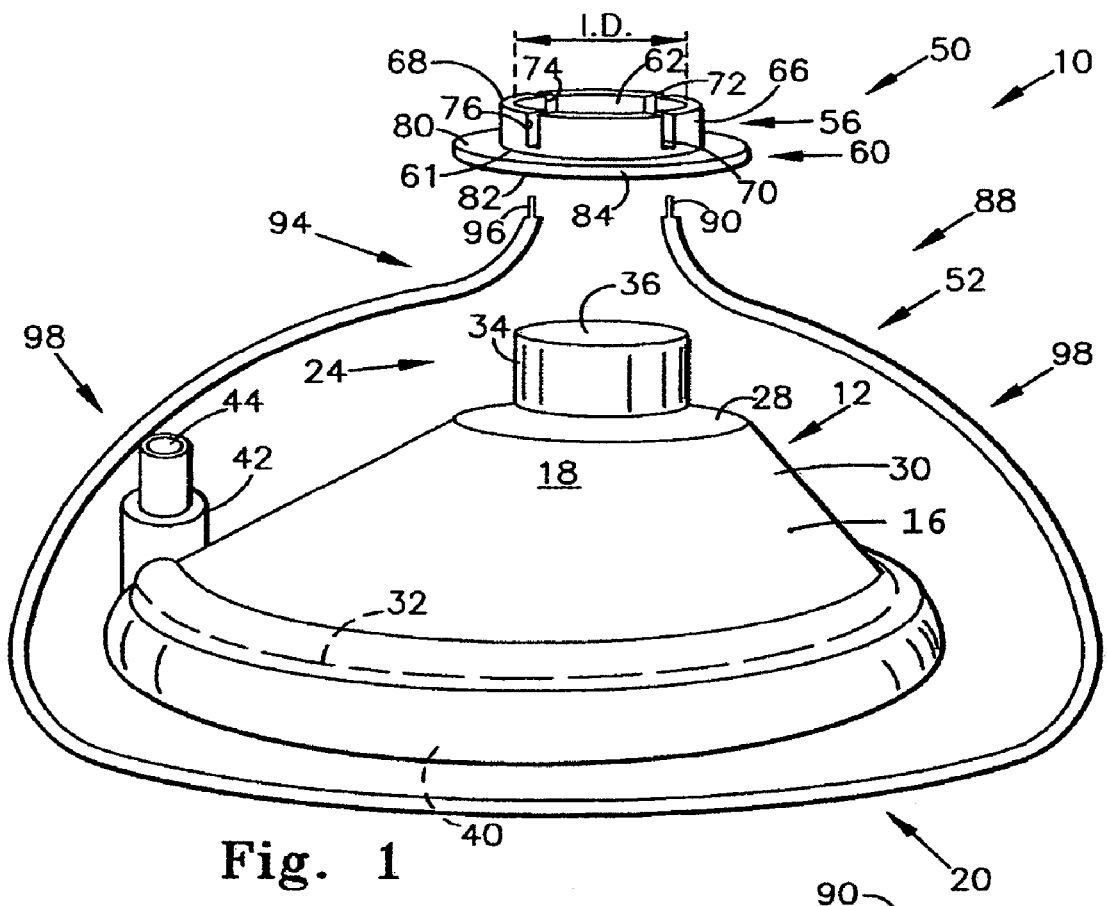
FIG. 1 is an exploded side view of the present invention.

A fourth embodiment strap system 500 is shown in FIGS. 12-14 and is designed to be used with a face mask 20 that is identical to face mask 20 of FIG. 1.

Strap system 500 includes a combination collar that is capable of being used with both the thin strap, such as strap 52, 206, that is shown in FIGS. 1 and 6; or alternately, a prior art wide strap, such as strap 330 as shown in FIG. 7. One of the primary benefits obtained from strap system 500 is that it both accommodates the new style strap 506, and prior art straps in one unit, so that the healthcare facility can maintain a single collar in inventory that will both address the preferences of those who prefer the smaller type strap (e.g. 52) and those practitioners who prefer the prior art wider strap 330.

The fourth embodiment strap system 500 includes a collar 504 and a strap 506. The collar 504 includes a generally cylindrical axially extending portion 510 that is sized generally similarly to the axially extending portion 56 of the first embodiment collar 50, and includes the slots 511 that are similar, if not identical in size, shape and placement to slots 70-76 of collar 50. The collar 504 also includes a radially extending portion 512 that is sized and positioned generally similarly to its counterpart in the first embodiment collar 50, and is joined to the cylindrical portion at a base line.

The generally cylindrical, axially extending portion 510 includes a radially inwardly facing surface 518 that defines an inner diameter ID that is preferably generally similar to the inner diameter ID of the first embodiment collar 50. The inner diameter ID defined by radially inwardly facing surface 518 is similarly sized to create a gap between the radially inwardly facing surface 518 and the gas port connector, through which the strap 506 can pass.

The slots 511 are sized for enabling the first and second end portions of the strap 506 to pass therethrough. Preferably, the slots 511 each have a length of approximately 0.27 in, (7.0 mm.), and a width of approximately 0.06 in. (1.6 mm.). The positioning of the slots 511 helps to facilitate locking the strap member 506 in a fixed position on the collar 502, when the strap end portions of the strap 506 are passed through appropriate slots. In this manner, collar 502 can be used in a manner similar to collar 50 of the embodiment shown in FIG. 1.

The collar 502 also includes four radially extending arms 517 that are disposed at evenly spaced (90°) intervals around the radial periphery of the collar 502 similar to prior art collar 314.

Each of the radially extending arms 517 includes an upstanding prong 519 that is disposed at the distal end of the respective radially extending arms 517. As alluded to above, the radially extending arms 517 are sized and positioned to receive the apertures of the first and second linear array of spaced apertures of a wide strap, such as strap 330 of FIG. 7.

The axially extending portion 510 also includes a radially outwardly facing surface, that terminates at an upper edge 524. The radially extending portion 512 includes an axially outwardly facing surface 526, and an axially inwardly facing surface 527, and terminates at a radially outwardly disposed outer edge 528.

The radially outwardly extending portion 512 includes first and second tabs 531, 533 that are preferably separated by approximately 180 degrees. The first and second tabs 531, 533 define first and second T-shaped slots 535, 537 for receiving the strap. Each of the first and second T-shaped slots 535, 537 include a first tab portion 540, and a second tab portion 542, that define therebetween, a laterally extending leg 544 of the T-shaped slots 535, 537, and a radially extending leg 546 of each of the first and second T-shaped slots 535, 537. It will be noted that the first and second tab portions 540, 542 are not joined at the radially outward most portions. As such, the tab portions 540, 542 define a gap 550 between the first and second tab portion 540, 542, so that the strap 506 can be moved laterally into engagement with the laterally extending leg 544 by placing the strap 506 along side the radially outermost part of the radially extending leg 546, and moving the strap 506 laterally through the gap 550, and in between the first and second tab portion 540, 542 until the strap 506 is seated within the laterally extending leg 544.

It will also be noted that the first and second tab portions 540, 542 extend radially outwardly further than the major circumferential radially outwardly facing surface 551 of the radially outwardly disposed outer edge 528. Each of the T-shaped slots 535, 537 are preferably sized so that the strap 506 will be snugly received within the laterally extending leg 544. When sizing the strap 506, and T-shaped slot 535, 537, the slots 535, 537 should be designed to be large enough to enable the strap 506 to pass therethrough without undue frictional resistance, but to still provide enough frictional resistance to prevent the strap 506 from being pulled out of the slots 535, 537 when the strap system 500 and face mask 20 are engaged on to the face of the user.

Having described the invention in detail with reference to certain preferred embodiments, it will be appreciated that the above description is not limiting, and is defined by the scope and spirit of the claims appended hereto.

What is claimed is:

1. A strap system for use with an anesthesia/respiratory face mask having an axially extending gas port connector having a first diameter, the strap system comprising
   a strap member having a first end portion, a second end portion and a middle portion connecting the first end portion and the second end portion, and
   a collar including an axially extending portion having a second diameter, the second diameter being sized, relative to the first diameter of the gas port connector, to define a gap between the axially extending portion of the collar and the axially extending gas port connector, the first and second end portions of the strap passing through the gap, and the gap being sized for snugly receiving the strap member.

2. The strap system of claim 1 wherein the axially extending portion of the collar includes at least two slots for receiving the strap member to fix the position of the strap member in the gap.

3. The strap system of claim 1 wherein the strap member has a width substantially greater than its thickness.

4. The strap system of claim 1 wherein the strap member has a rest length and is comprised of an elastic material that has sufficient elasticity to enable the length of the strap member to be increased by at least fifty percent from its rest length.

5. The strap system of claim 1 where the collar includes a radially extending portion placeable against the face mask.

6. The strap system of claim 4 wherein the strap member has a shoe string-like size and shape.

7. The strap system of claim 1 wherein the difference between the first diameter and the second diameter is between about 1.4 and 2.0 millimeters.

8. The strap system of claim 7 wherein the strap member has a width substantially greater than its thickness.

9. The strap system of claim 8 wherein the axially extending portion of the collar includes at least two slots for receiving the strap member in the gap.

10. The strap system of claim 9 wherein the at least two slots have a length of between about 6.0 and 9.0 millimeters, and a width of between about 1.0 and 3.0 millimeters.

11. The strap system of claim 1 further including a gasket member, the gasket member being coupled to the face mask and engagable and conformable to a face of a patient, wherein the gasket member comprises an air bladder having an air valve for adjusting air pressure within the air bladder.

12. A strap system for use with an anesthesia/respiratory face mask having an axially extending gas port connector having a first diameter and a gasket member engagable with and conformable to a face of a patient, the strap system comprising:
    a strap member having a first end portion, a second end portion and a middle portion; and
    a collar including a radially extending portion and having at least a first and a second slot through which the first and second end portions of the strap member can pass, the first and second slots being sized for adjustably receiving and fixedly positioning the first and second end portions of the strap member,
    wherein the radially extending portion includes first and second radially outwardly extending tab members, the at least first and second slots being disposed on the respective first and second tab members,
    wherein the strap member includes a plurality of apertures, and the collar further includes at least two radially extending arms, the at least two radially extending arms sized and positioned for receiving at least two of the plurality of apertures to adjustably receive and fixedly position the strap member to the collar, and
    wherein the collar further includes an axially extending portion having a second diameter, the second diameter being sized relative to the first diameter of the gas port connector to define a gap between the axially extending portion of the collar and the axially extending portion of the gas port connector, the gap being sized for snugly receiving the strap member.

13. A strap system for use with an anesthesia/respiratory face mask having an axially extending gas port connector having a first diameter, and a gasket member engageable with and conformable to a face of a patient, the strap system comprising
    a strap having a first end portion, a second end portion and a middle portion, the strap having a width substantially greater than its thickness, and a rest length, the strap being comprised of an elastic material that has sufficient elasticity to enable the length of the strap to be increased by at least ten percent from its rest length and
    a collar including a radially extending portion and an axially extending portion, the axially extending portion having a second diameter sized for internally receiving the gas port connector, the second diameter being sized, relative to the first diameter to define a gap between the axially extending portion of the collar and the axially extending portion of gas port connector, the gap being sized for snugly receiving the strap between the collar and the gas port connector, the radially extending portion of the collar including at least a first and a second radially outwardly extending tab member, the first and second tab members defining respectively, a first and a second T-shaped slot capable of receiving and fixedly positioning the strap therein, and at least two radially extending arms sized and positioned for being capable of receiving apertures of an aperture containing strap member.

* * * * *